(12) United States Patent
Seder et al.

(10) Patent No.: US 7,520,897 B2
(45) Date of Patent: Apr. 21, 2009

(54) MEDICAL DEVICES HAVING ANTIMICROBIAL PROPERTIES

(75) Inventors: Edmund V. Seder, Santa Barbara, CA (US); Jesse N. Nelson, Oxnard, CA (US)

(73) Assignee: Helix Medical, LLC, Plymouth, MI (US)

( * ) Notice: Subject to any disclaimer, the term of this patent is extended or adjusted under 35 U.S.C. 154(b) by 549 days.

(21) Appl. No.: 10/990,168

(22) Filed: Nov. 15, 2004

(65) Prior Publication Data

US 2005/0256573 A1 Nov. 17, 2005

Related U.S. Application Data

(63) Continuation-in-part of application No. 09/833,961, filed on Apr. 11, 2001, now abandoned, and a continuation-in-part of application No. 10/487,614, filed as application No. PCT/US02/41274 on Dec. 20, 2002, now Pat. No. 6,948,526.

(60) Provisional application No. 60/344,444, filed on Dec. 28, 2001.

(51) Int. Cl.
*A61F 2/20* (2006.01)
(52) U.S. Cl. ............... 623/9; 623/23.68; 623/26; 424/404; 424/457
(58) Field of Classification Search .............. 623/9, 623/23.68, 26, 926; 424/404, 457
See application file for complete search history.

(56) References Cited

U.S. PATENT DOCUMENTS

| | | | |
|---|---|---|---|
| 3,445,420 A | 5/1969 | Kookootsedes et al. | |
| 3,932,627 A | 1/1976 | Margraf | |
| 3,932,629 A | 1/1976 | Dawes et al. | |
| 3,952,335 A | 4/1976 | Sorce et al. | |
| 4,040,428 A | 8/1977 | Clifford | |
| 4,054,139 A | 10/1977 | Crossley | |

(Continued)

FOREIGN PATENT DOCUMENTS

DE 19754432 6/1999

(Continued)

OTHER PUBLICATIONS

"Biofilm Formation In Vivo on PerfluroAlkylsiloxane-Modified Vocie Prostheses", Everaert et al., Arch Otolaryngol Head Nec Surg. 1999;125:1329-1332.*

(Continued)

*Primary Examiner*—N. Bhat
(74) *Attorney, Agent, or Firm*—Ronald W. Wangerow; Harness, Dickey & Pierce, PLC

(57) ABSTRACT

Microbial growth on the surface of a valve of a voice prosthesis and optionally the cartridge or ring supporting the valve, is inhibited by providing antimicrobial activity at a level sufficient to retard growth of a microbial film by dispersing an inorganic antimicrobial agent such as silver oxide or an organic antimicrobial agent such as triclosan or butyl paraben dispersed in a medical grade silicone elastomer. The valve, ring or cartridge is in contact with body fluids containing microorganisms and nutrients therefor. The antimicrobial surface can interfere with or inhibit the growth of a biofilm, bacterial layer or a yeast layer. The body of the prosthesis may also contain an antimicrobial surface as long as it is non-toxic to the tissue it contacts.

16 Claims, 8 Drawing Sheets

U.S. PATENT DOCUMENTS

| | | | |
|---|---|---|---|
| 4,435,853 A | 3/1984 | Blom et al. | |
| 4,483,688 A | 11/1984 | Akiyama | |
| 4,563,485 A | 1/1986 | Fox, Jr. et al. | |
| 4,581,028 A | 4/1986 | Fox, Jr. et al. | |
| 4,592,920 A | 6/1986 | Murtfeldt | |
| 4,603,152 A | 7/1986 | Laurin et al. | |
| 4,610,691 A | 9/1986 | Depel et al. | |
| 4,612,337 A | 9/1986 | Fox, Jr. et al. | |
| 4,615,705 A | 10/1986 | Scales et al. | |
| 4,677,143 A | 6/1987 | Laurin et al. | |
| 4,911,716 A | 3/1990 | Blom et al. | |
| 5,019,096 A * | 5/1991 | Fox et al. | 600/36 |
| 5,064,433 A | 11/1991 | Blom et al. | |
| 5,238,749 A | 8/1993 | Cueman et al. | |
| 5,314,470 A | 5/1994 | Persson | |
| 5,391,205 A | 2/1995 | Knight | |
| 5,474,797 A | 12/1995 | Sioshansi et al. | |
| 5,480,432 A | 1/1996 | Suding et al. | |
| 5,507,809 A * | 4/1996 | Blom | 623/9 |
| 5,520,664 A | 5/1996 | Bricault, Jr. et al. | |
| 5,567,495 A | 10/1996 | Modak et al. | |
| 5,578,083 A * | 11/1996 | Laguette et al. | 623/9 |
| 5,624,704 A | 4/1997 | Darouiche et al. | |
| 5,632,775 A | 5/1997 | Suding et al. | |
| 5,693,097 A | 12/1997 | Laguette et al. | |
| 5,772,640 A | 6/1998 | Modak et al. | |
| 5,902,283 A | 5/1999 | Darouiche et al. | |
| 5,928,569 A * | 7/1999 | Reo | 252/514 |
| 5,957,978 A * | 9/1999 | Blom | 623/9 |
| 6,013,711 A | 1/2000 | Lewis et al. | |
| 6,017,587 A | 1/2000 | Kleyer et al. | |
| 6,083,208 A | 7/2000 | Modak et al. | |
| 6,106,505 A * | 8/2000 | Modak et al. | 604/265 |
| 6,358,222 B1 | 3/2002 | Grundei | |
| 6,361,526 B1 * | 3/2002 | Reisdorf et al. | 604/265 |
| 6,558,686 B1 | 5/2003 | Darouiche | |
| 6,596,401 B1 | 7/2003 | Terry et al. | |
| 6,689,302 B2 | 2/2004 | Reisdorf et al. | |
| 6,716,895 B1 * | 4/2004 | Terry | 523/122 |
| 6,887,270 B2 * | 5/2005 | Miller et al. | 623/11.11 |
| 6,948,526 B2 * | 9/2005 | Seder et al. | 137/855 |
| 7,081,133 B2 * | 7/2006 | Chinn et al. | 623/2.41 |
| 2002/0022136 A1 | 2/2002 | Valade et al. | |
| 2002/0193879 A1 | 12/2002 | Seder et al. | |
| 2004/0116551 A1 | 6/2004 | Terry | |
| 2004/0187941 A1 | 9/2004 | Seder et al. | |
| 2004/0214939 A1 | 10/2004 | Patel et al. | |
| 2005/0020844 A1 | 1/2005 | Nelson | |
| 2005/0049350 A1 | 3/2005 | Tonapi et al. | |
| 2005/0148721 A1 | 7/2005 | Tonapi et al. | |
| 2005/0161859 A1 | 7/2005 | Miller et al. | |
| 2005/0239940 A1 | 10/2005 | Shima et al. | |
| 2005/0256573 A1 | 11/2005 | Seder et al. | |
| 2006/0045899 A1 | 3/2006 | Sarangapani | |
| 2006/0047043 A1 | 3/2006 | Nakayoshi et al. | |

FOREIGN PATENT DOCUMENTS

| | | | |
|---|---|---|---|
| EP | 0 222 509 | * | 5/1987 |
| EP | 0222509 | | 5/1987 |
| WO | WO 97/14447 | * | 4/1997 |
| WO | WO 97/45075 | | 12/1997 |
| WO | WO 98/04463 | | 2/1998 |
| WO | WO 98/08463 | * | 3/1998 |
| WO | WO 01/43788 | | 6/2001 |
| WO | WO 02/077095 | | 10/2002 |
| WO | WO 02/083031 | | 10/2002 |
| WO | WO 03/057083 | | 7/2003 |
| WO | WO 03/082983 | | 10/2003 |
| WO | WO 2004/017738 | | 3/2004 |
| WO | WO 2004/046233 | | 6/2004 |
| WO | WO 2004/050753 | | 6/2004 |
| WO | WO 2005/014074 | | 2/2005 |
| WO | WO 2005/087135 | | 9/2005 |

OTHER PUBLICATIONS

Everaert et al. "Biofilm Formation In Vivo on PerfluoroAlkylsiloxane-Modified Voice Prostheses" Arch Otolaryngol Head Neck Surg. vol. 125, Dec. 1999. pp. 1329-1332.

Saidi et al. "In Vivo Resistance to Bacterial Biofilm Formation on Tympanostomy Tubes as a Function of Tube Material" Otolaryngology-Head and Neck Surgery. vol. 120, No. 5, pp. 621-627 (1999)—Abstract only.

* cited by examiner

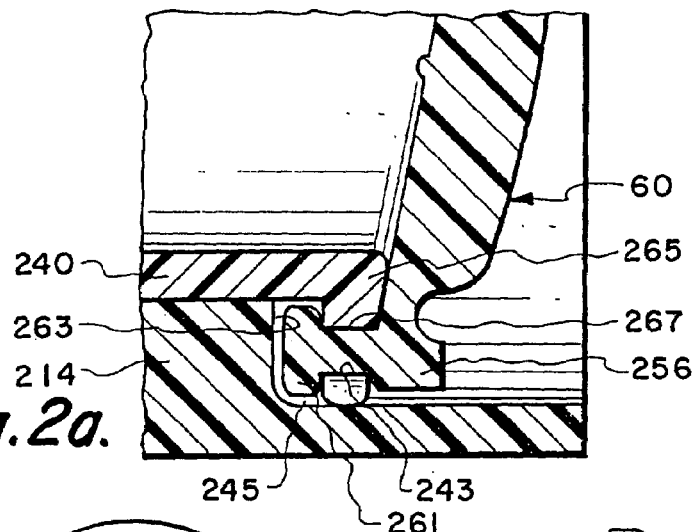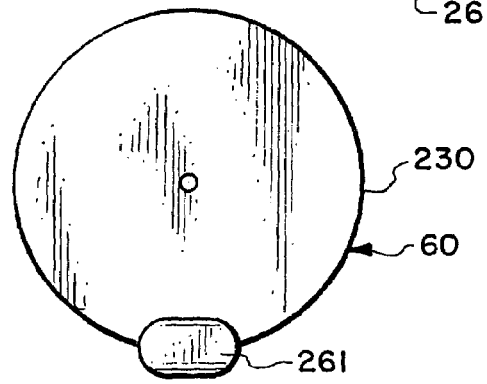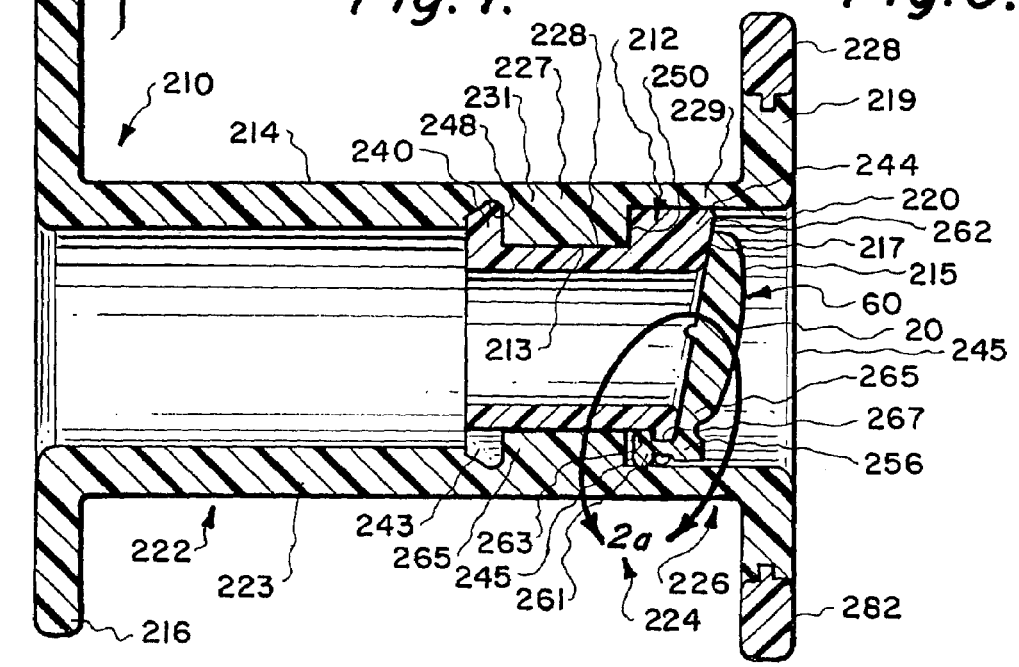

CARTRIDGE INDWELLING VOICE PROSTHESIS
RING VALVE DESIGN

MEDICAL DEVICES HAVING ANTIMICROBIAL PROPERTIES

CROSS-REFERENCE TO RELATED APPLICATIONS

This application is a continuation-in-part of Ser. No. 10/487,614 filed Feb. 19, 2004 (issued Sep. 27, 2005 as U.S. Pat. No. 6,948,526), which is a national phase filing of PCT/US02/41274 filed Dec. 20, 2002, which claims benefit of U.S. provisional application Ser. No. 60/344,444 filed Dec. 28, 2001; and is a continuation in-part of Ser. No. 09/833,961 filed Apr. 11, 2001.

TECHNICAL FIELD

The present invention relates to microbial-resistant medical devices and, more particularly, this invention relates to a voice prosthesis having a valve which retards growth of microbial organisms.

BACKGROUND OF THE INVENTION

Medical devices, particularly synthetic resin prosthetic devices which are used in environments where micro-organisms such as fungi or yeast and/or bacteria are actively growing, can become covered with a biofilm colonized layer to the point where the function of the device is impaired. After growth of the biofilm microbial layer, filaments can grow and descend into the body or wall of the polymeric device and detrimentally affect its physical properties until the device no longer functions. The fouled device must be cleaned or discarded.

Whenever a prosthesis is in contact with moisture in a warm, dark environment, the surfaces are subject to microbial growth, usually containing a predominant amount of *Candida* usually mixed with bacteria. The microbial growth can interfere with the functioning of the prosthesis, requiring removal of the prosthesis for disposal or cleaning. The microbial growth is a persistent problem in the management and care of patients who have had their larynx removed and utilize a voice prosthesis since the prosthesis is exposed to a non-sterile, humid, warm, nutrient rich environment.

There are several options for restoring speech to patients who have had their larynx removed. One procedure is to surgically create a puncture or fistula between the trachea and the esophagus. A tracheoesophageal voice prosthesis containing a one-way valve such as a BLOM-SINGER® voice prosthesis is inserted into the tracheoesophageal fistula. The one-way valve protects the airway during swallowing but opens under positive pressure from the trachea. The voice prosthesis, thus, permits a patient to divert air from the lungs into the esophagus and out through the mouth. Speech is created during passage of air through the upper part of the esophagus.

The prosthesis maintains the fistula open, transfers air from the trachea to the esophagus for voice production and prevents esophageal leakage into the trachea during swallowing. The oral cavity which extends into the throat has a high microbial population. However, the prosthesis being in contact with moisture in a warm, dark, nutrient rich environment is subject to growth of commonly found micro-organisms, typically *Candida* on the valve and the retaining flange. The microbial attack is currently being studied. The microbial attack organisms and sequence of events are quite complex and are still undetermined. The microbial growth on and into the soft silicone resin can interfere with function of the valve and can cause the flange to wrinkle and the valve to leak. The fouled device must be cleaned or discarded and replaced with a new device.

One type of current low pressure voice prosthesis can be removed by the patient every few days and can be replaced with a clean prosthesis. The removed prosthesis is soaked in hydrogen peroxide to sterilize and clean the valve and flange. Some patients however, have difficulty managing frequent removal and reinsertion of the prosthesis. Others, who are physically handicapped are not able to remove, sterilize, or reinsert the prosthesis.

A longer dwelling, low pressure voice prosthesis has been developed that can remain in place in the tracheoesophageal fistula for many weeks or months, depending on the patient and conditions of use. The patient can confidently use the prosthesis for longer periods. The longer dwelling voice prosthesis is not removable by the patient. Trips to a health care specialist to remove and replace the prosthesis are greatly extended providing increased comfort and lower cost to the patient.

Another type of soft voice prosthesis includes a rigid stiffening ring 14 inserted into a groove in the soft body of the prosthesis. Though the ring stiffens the body adjacent the valve it does not prevent distortion of the body by muscular movement or distortion of the valve by growth of yeast.

U.S. Pat. No. 5,578,083 issued Nov. 26, 1996, discloses the use of a stiff cartridge to support the soft silicone prosthesis and to provide a seat for the valve which is connected to the cartridge by a tab in slot design. Another cartridge-valve design includes a one piece sleeve-valve which is stretched over and seats in a cylindrical groove in the cartridge as disclosed in U.S. Ser. No. 10/487,614, filed Feb. 19, 2004, the disclosure (051) of which is incorporated herein by reference. However, microbial growth can still proceed to a point at which the valves can not be reliably sealed.

Microbial growth on the valve can also cause distortion of the shape of the valve or form wrinkles in the body of the valve which prevents the valve from closing. Leaking also appears to be due to distortion of the valve body adjacent to the seat of the valve and to microbial growth on the seat. Forming the valve with an arcuate dome shape increased resistance to folding or bending of the valve. However, some valves still leaked after extended placement in a fistula.

The use of silicone elastomer is limiting because of the open matrix nature of the material. The open nature of silicone allows microorganisms to attach to and sometimes burrow through the material. The attachment of microorganisms at the valve seat interface can interfere with creating a seal. Attachment of microorganisms to the flexible hinge area can reduce the flexibility of the hinge, and can also be a precursor for other microorganisms to burrow into the silicone, effectively changing the shape of the silicone and thereby interfering with the ability for the valve to seal correctly. In extreme cases, microorganisms can attach and burrow into the esophageal side of the valve to the point where the sealing seat of the valve is altered in shape.

Historically, microbial ingrowth resistance has come from selection of hard plastics and metals that reduce attachment of microorganisms to certain components. These materials were restricted from use in the hinge area and other areas that required flexibility and resilience. The components requiring this flexibility and resilience have traditionally been molded from silicone elastomer.

In other medical devices, antimicrobial coatings have been available for some years. Coatings typically do not last the lifetime of the product on the highly flexible hinge, as the coating tends to flake off. Once this happens, the hinge is left unprotected and is exposed to the effects of microorganisms.

Application of antimicrobial substances to silicone articles can also come by way of solvent introduction. In this method, the silicone part is soaked with a solvent containing a dissolved antimicrobial agent. The silicone part is removed from the solvent and the solvent is allowed to evaporate. The dissolved antimicrobial agent is then deposited in the matrix of the silicone elastomer. There are several variations of this method. This method is limited to antimicrobial agents that are soluble in an effective solvent and to the uncertainty of exact load level. This method also requires the additional steps and regulations associated with working with solvents.

The use of polymers having antimicrobial properties is disclosed in PCT Publication No. WO98/04463 published March 1998. Through the voice prosthesis device formed of flurosilicone polymer showed same initial success, examination of returned devices from a clinical study showed significant microbial growth on both the posterior aspect and periphery of the valve flap and on the inner surface of the valve hood which interfered with movement of the valve flap. Any further use of the flurosilicone device was abandoned.

List of Prior Art

| Patent No. | Patentee |
| --- | --- |
| 3,932,627 | Margraf |
| 4,054,139 | Crossley |
| 4,483,688 | Akijama |
| 4,563,485 | Fox, Jr. et al. |
| 4,581,028 | Fox, Jr. et al. |
| 4,603,152 | Laurin, et al. |
| 4,612,337 | Fox, Jr. et al. |
| 4,615,705 | Scales et al. |
| 5,019,096 | Fox, Jr. et al. |
| 5,567,495 | Modak et al. |
| 5,624,704 | Darouiche et al. |
| 5,772,640 | Modak et al. |
| 5,902,283 | Darouiche et al. |
| 6,083,208 | Modak et al. |
| 6,106,505 | Modak et al. |

Statement of Prior Art

Margraf discloses the use of a silver-heparin-allantoin complex to a form non-thrombogenic, self sterilizing surface on prosthetic valves or arterial grafts. The complex can be coated or impregnated into the surface of the valve or graft.

Crossley coats the surface of an urinary tract catheter with Ag or Ag compounds by dispersing silver or its compound in resin. The surface is abraded to expose the silver material. The coating contains 10% by weight of silver (col 4, line 10). The coating can be extremely thin such as those deposited by electroless deposition (col 4, lines 16-18).

Fox, Jr. et al., U.S. Pat. No. 4,563,485 discloses use of silver norfloxacin or silver perfloxacin to render muscular graft prosthesis formed from resins such as silicone infection resistant.

Fox, Jr. et al., utilizes silver metal salts of sulfonamides or other antimicrobials for the same purpose.

Fox, Jr. et al., discloses and claims a method of preparing an infection resistant material by solvent impregnation of the material with a silver salt and another compound and reaction in situ to form a silver salt.

Scales et al., provides a bioerodible silver coating on the surface of endoprosthetic orthopaedic implants to render the surface antimicrobial.

Fox, Jr. et al., discloses the use of a complex of a silver salt and chlorhexidine to add antimicrobial properties to biomedical polymers such as silicones.

Laurin, et al. discloses mixing an oligodynamic material such as a salt of silver, gold, platinum, copper or zinc with a resin to form an antimicrobial coating for catheters.

Akijama coats an oligodynamically active silver, gold or copper salt on the periphery of a tubular catheter.

Modak et al. and Darouiche et al. discloses the use of triclosan to silicone medical devices such as catheters to inhibit microbial growth. By coating the agent onto the surface of the device or soaking the device in swelling agent and then in a solution containing triclosan to introduce triclosan into the device.

When soft prosthesis were compounded with antimicrobial agents such as silver compounds at a level which resists growth of microorganisms, it was discovered that the prosthesis was irritating to and/or toxic to tissue in contact with the prosthesis.

Statement of the Invention

It has been discovered in accordance with the present invention that antimicrobial agents can be compounded into parts of a prosthetic that are not in contact with tissue. The antimicrobial parts will be free of microbial growth for an extended period which contributes to longer use of the prosthesis in vivo. For example, the valve in most voice prostheses is not in contact with tissue. It is only in intermittent contact with body fluids. The same is true of the inside surface of the tubular prosthesis and/or the facial and inside surfaces of rings or cartridges present to reinforce the soft body of a prosthesis. By adding an amount of microbial agent effective to resist growth onto or into the valve, ring or cartridge it is found that microbial growth is delayed for a significant period without any evidence of irritation or toxicity to the tissue.

The isolation of the valve from tissue is enhanced by recessing the valve forward of the rearward edge of the prosthesis and/or forward of a flange which seats the prosthesis in a tracheoesophageal fistula.

The body of the prosthesis may have some antimicrobial properties as long as the surface of the body is not toxic to tissue. For example, the body can be formed of a polyurethane polymer which resists attachment of a biofilm or a microbial layer.

The antimicrobial agent can also be compounded by dispersion into the raw material. For example, silicone elastomer can contain up to 100 phr of an antimicrobial agent such as silver or silver compounds such as silver oxide suitably about 5 up to less than 50 phr of silver oxide. Other suitable antimicrobial compounds toxic to tissue can be used in the non-tissue contact regions such as gold, platinum, copper, zinc metal powder or oxides and salts thereof.

However, it has been discovered that metal oxides such as silver oxide accelerate the curing of silicone elastomers used to form the valve leading to uneven dispersions and short pot life. In accordance with the invention, the pot life of silicone valves containing silver oxide can be increased by adding a curing inhibitor to the composition before cure in an amount of at least of 1 mole of inhibitor to 6 moles of $Ag_2O$. The pot life is increased to 4-8 hours and the dispersion of the $Ag_2O$ powder is uniform throughout the valve by adding 2 drops of inhibitor per 100 grams of silicone elastomer such as NuSil.

Preferred organic antimicrobial agents that can be added to the valve are organic antimicrobial agents that can be dispersed throughout the silicone raw material preferably a food grade preservative such as an aromatic carboxylic acid or $C_1$ to $C_9$ ester thereof such as butyl paraben (butyl p-hydroxy Benzoate) or an alkene carboxylic acid salt such as alkali metal sorbate salt or a halohydroxy aromatic ether such as triclosan (2,4,4'-trichloro-2'-hydroxydiphenyl ether). Organic antimicrobial agents can be selected from the group consisting of unsaturated aliphatic acid salt, halogenated hydroxy aromatic acids, esters thereof, and aromatic ethers.

The agents can be dispersed throughout the silicone by milling a dry powder into liquid resin before curing by pre-dissolving in minimum amount of solvent and then mixing or milling the solution into the liquid resin or heating the agent above its melting temperature but below its decomposition temperature and mixing the molten material with the liquid resin before molding. The agents were chosen to be sufficiently robust to survive the molding process.

The hard cartridges or rings are suitably formed of a hard engineering plastic such as Kynar. The cartridges can also contain a uniform dispersion of an organic antimicrobial agent as disclosed above.

Valves and cartridges for voice prosthesis have been compounded with a dispersion of antimicrobial agents and were subjected to in vitro and in vivo testing. The valves and cartridges are found to exhibit significant inhibition of microbial growth. The presence of the antimicrobial agent throughout the matrix will retard both surface attachment and penetration of microorganisms into the valve.

Another aspect of the invention is to prevent unseating of the valve distortion, of the valve and/or cartridge due to muscle action of the stoma and to further isolate the valve from microorganisms carried by saliva. In accordance with the invention a metal sleeve suitably formed of titanium surrounds the portion of the cartridge supporting the valve and its attachment means.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 2 is a view in section of an assembly of the valve, cartridge and body of an embodiment of the voice prosthesis of the invention;

FIG. 2a is an enlarged sectional view of the valve securing means shown in FIG. 2 for purposes of clarity;

FIG. 3 is a side view in elevation of the valve shown in FIG. 2;

FIG. 4 is a front view in elevation of the valve shown in FIG. 2;

DETAILED DESCRIPTION OF THE INVENTION

The invention will be illustrated by two embodiments of a long-dwelling voice prostheses with hard cartridge and a soft body voice prosthesis, though it is applicable to any prosthetic or medical device disposed in a body cavity having an environment conducive to growth of micro-organisms such as *Candida Albicans*.

Figure 1:
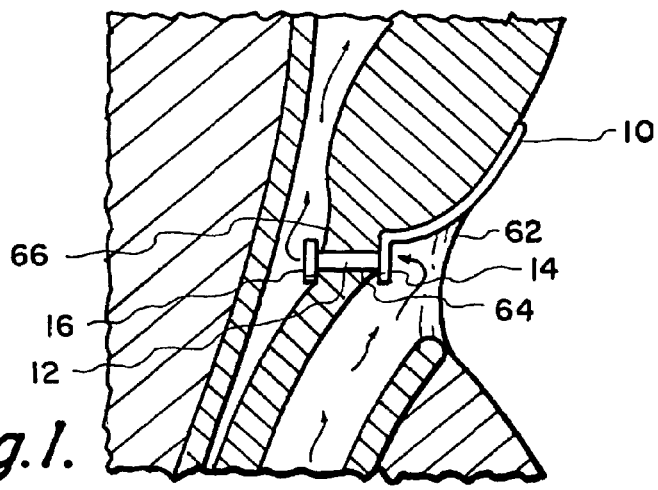
FIG. 1 is a schematic view of a voice prosthesis installed in a tracheoesophageal fistula.
Figure 5:
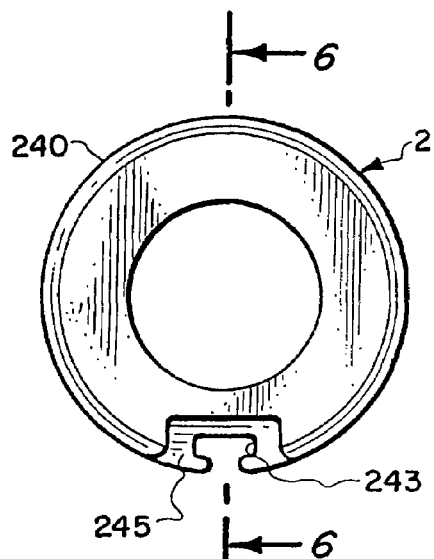
FIG. 5 is a rear view in elevation of the cartridge shown in FIG. 2.
Figure 6:
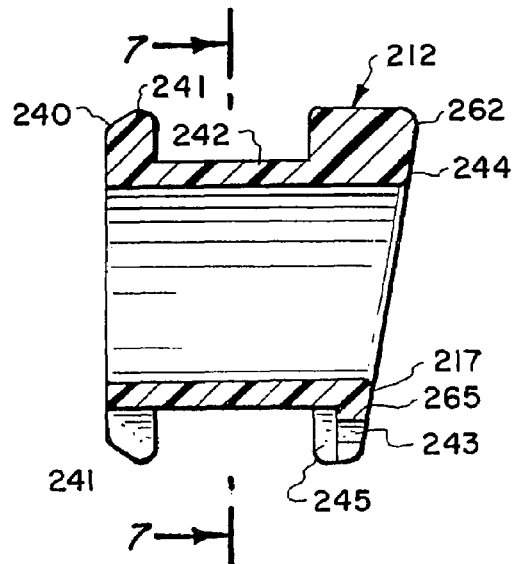
FIG. 6 is a view in section taken along line 6-6 of FIG. 5.
Figure 7:
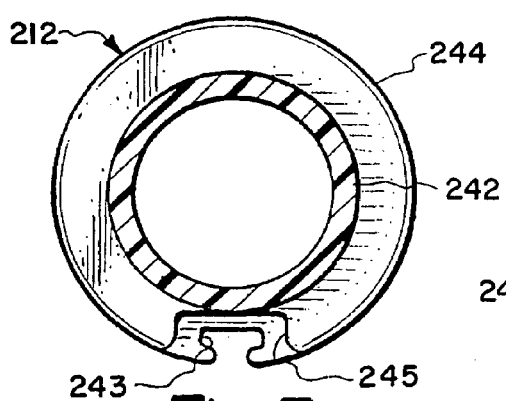
FIG. 7 is a view in section taken along line 7-7 of FIG. 6.
Figure 8:
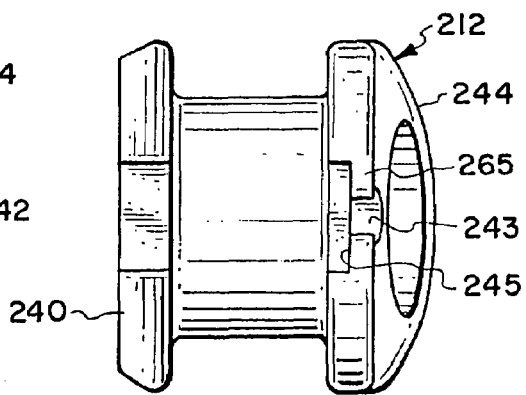
FIG. 8 is a bottom view in elevation of the cartridge illustrated in FIG. 2.
Figure 9:
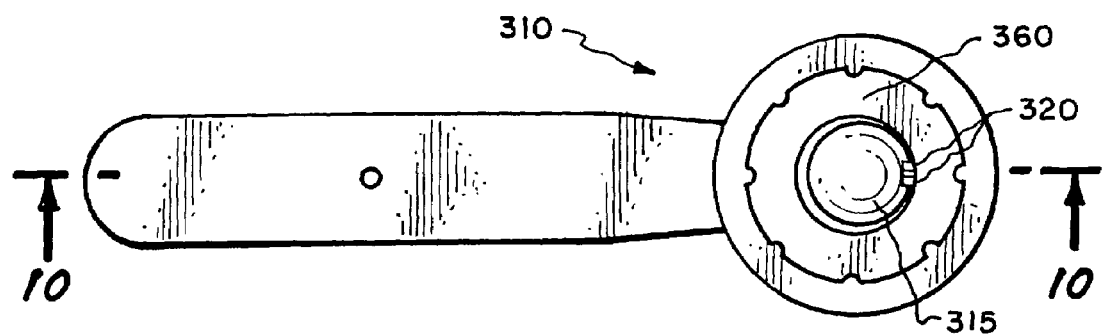
FIG. 9 is a top view in elevation of the prosthesis illustrated in FIG. 9.
Figure 10:
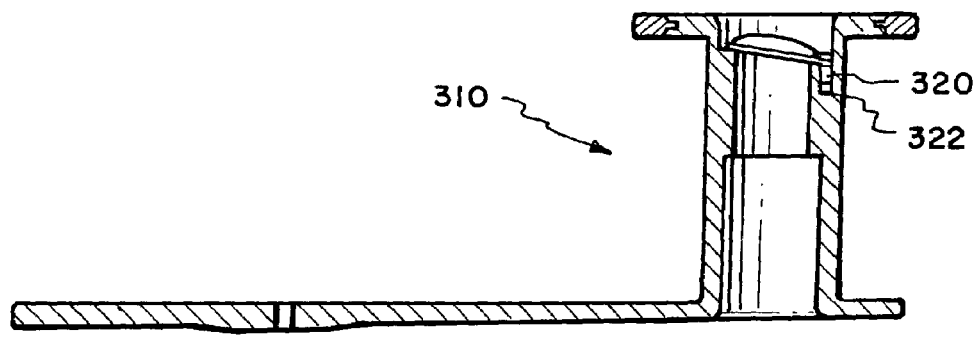
FIG. 10 is a view in section taken along line 10-10 of FIG. 9.
Figure 11:
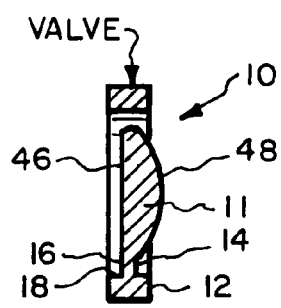
FIG. 11 is a view in section of a second embodiment of valve with seating band according to the invention.
Figure 13:
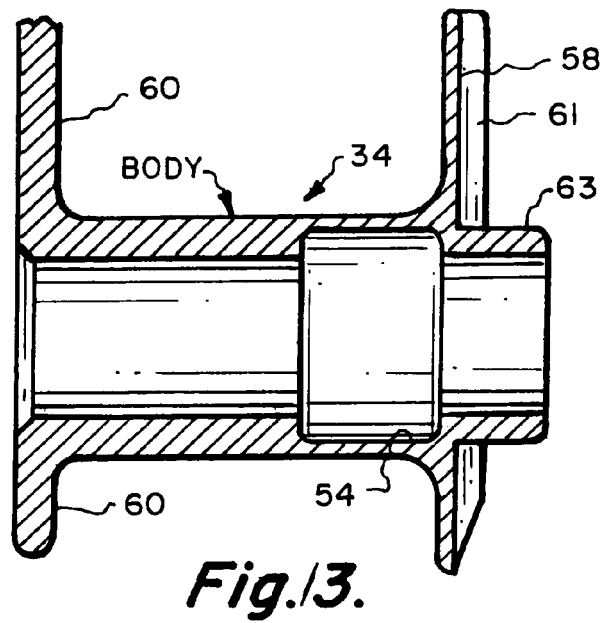
FIG. 13 is a view in section of a soft body for a voice prosthesis according to the invention.
Figure 12:
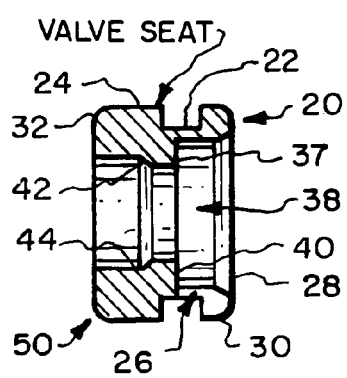
FIG. 12 is a view in section of a hard cartridge with valve seat according to the invention.
Figure 14:
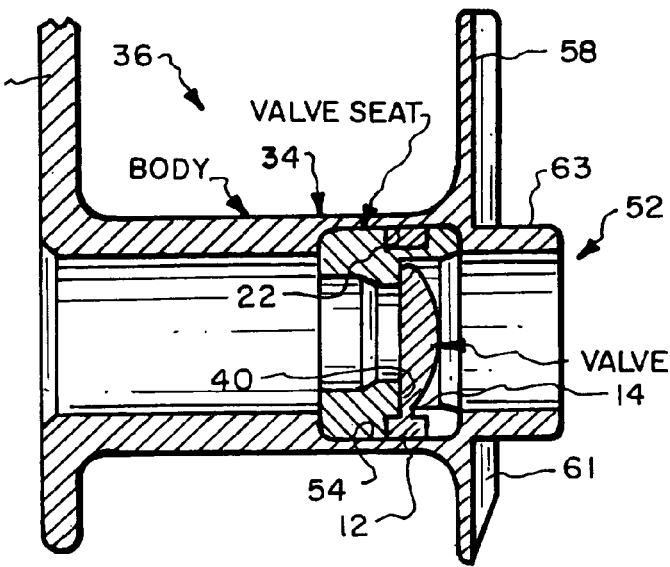
FIG. 14 is a view in section of the assembly of the body, cartridge and valve illustrated in FIGS. 11-13.

Referring now to FIGS. 1 and 8-9, a first embodiment of a voice prosthesis 10 is shown inserted into a fistula 62 with the front flange 14 engaging the outer wall 64 of the trachea and the rear flange 16 engaging the wall 66 of the esophagus. The body 12 of the prosthesis 10 prevents the fistula 62 from closing. The body 12 and flanges 14, 16 are formed of an elastomer material which is non-toxic to tissue. The prosthesis 10, 310 also contains a valve 60, 360 as shown in FIGS. 2-4 and FIGS. 8, 9 which has an antifungal surface 215, 315 toxic to tissue. The valve 60, 360 is preferably separately molded and has a flap 20 or 2 posts 320 which are attached to the prosthesis 10, 310. In the soft prosthesis 310, the posts 320 are received in cavities 322 in the body and secured thereto by potting with a biocompatible adhesive such as RTV. The valve could also be mounted in a rigid sleeve attached to the distal end of the cartridge.

Referring again to FIGS. 2-4, a long dwelling prosthesis 210 can further contain an internal, rigid cartridge 212 which reinforces the body 214 of the soft prosthesis as shown in FIGS. 2-8 and as disclosed in U.S. Pat. No. 5,578,083 the disclosures of which are expressly incorporated herein by reference.

Referring particularly now to FIGS. 2 and 2a, a preferred voice prosthesis 210 is formed of a tubular body 214, a hollow, rigid cartridge 212 received in a channel 213 through the body 214 and a flapper valve 215 mounted on the rear face 217 of the cartridge 212.

A front tracheal flange 216 and a rear retention esophageal flange 219 are connected to the ends of the body 214. A flexible tab 218 can be attached to the front flange 216. The tab 218 can contain an aperture 221 which can be connected to an insertion tool, not shown. The body 214, front flange 216 and rear flange 219 are preferably a single molded, unitary structure formed from a biocompatible elastomer such as silicone resin, suitably a 50 durometer, medical grade, silicone elastomer. Since the resin is transparent and the prosthesis structure is small, the prosthesis is difficult to visualize and handle. Therefore, the molding resin generally, but not always, can contain a small amount, from 0.1 to 0.5% of a biocompatible pigment to aid in seeing the device. The pigment can be a heavy metal salt such as barium sulfate. The cartridge 212 can be formed of an inert, self-lubricating thermo plastic polymer, a fluorinated resin such as KYNAR, a semi-crystalline, low molecular weight polymer of vinylidine fluoride, such as TEFLON (polytetrafluoroethylene) or a polyalkylene resin such as polyethylene or polypropylene.

The tubular body 214 has a first section 222 having a wall 223 of a first thickness, a central section 224 having a wall 227 of a greater thickness and a third wall section 226 having a wall 229 of reduced thickness. The central wall section 224 forms a cylindrical boss 231 which is received in an annular channel 228 formed in the outer wall of the cartridge 212.

The hollow cartridge 212 has a front flange 240, a rear flange 244 forming a central channel 242 between the flanges 240, 244. The cartridge 212 is assembled with the body 214 by inserting the front flange 240 of the cartridge 212 into the rear opening 245 of the body 214 and forcing it through the central channel 213 of the body compressing the boss 231 until the front flange 240, seats against the end wall 248 of the boss 231 and the rear flange 244 seats against the rear wall 250 of the boss 231.

Referring now to FIGS. 3 and 4, the rear flange 244 has a horizontal slot 243 for receiving a tab 232 mounted on the front face of the valve 60 which communicates with an enlarged recess 245. The remaining volume in the recess 245 can be filled with biocompatible adhesive such as a silicone adhesive. Preferably, the tab 232 contains a bulbous end 261 which seats in the recess 245. The rear face 262 of the rear flange 244 can be angled to the vertical in order to preload the valve 60. Usually the angle is form 1 to 20 degrees, preferably 3 to 10 degrees.

Referring further to FIGS. 3 and 4, the flapper valve 60 has a round segment 230 connected to an attachment flap 256. A live hinge 234 in the form of a score line separates the segment 230 from the flap 256. A tab 232 is provided on the flap 256 for attaching the valve 60 to the body of the cartridge 212.

The hinge is located adjacent the lower, recessed portion of the rear face of the flange 244 which preloads the valve 60. The valve 60 is further strengthened by the increased thickness of the dome-shaped rear face 280 of the round segment 230. Leakage of the valve is further decreased due to the seating of the valve element 60 on the hard, smooth outer surface 217 of the rear flange 244 of the cartridge.

In order to assure that the rear flange 219 of the body 214 is fully seated on the esophageal wall surrounding a fistula, a narrow opaque ring 282 can be attached to or molded into the rear flange 219 as disclosed in U.S. Pat. No. 5,480,432 on Jan. 2, 1996, the disclosure of which is expressly incorporated herein by reference. An opaque pattern can also be provided by depositing opaque dots such as tantalum on the flange. The ring 282 has a width at least 10% the diameter of the rear flange usually from 10% to 50% the diameter of the annular rear flange. Usually the rear flange has a diameter of about 0.5 inch and the ring has a width of about 0.05 to 0.10 inch. The ring 282 preferably has an outer perimeter coincident with that of the rear flange 219 so that folds anywhere on the rear flange will be detected by the displayed image of the ring 282. The ring is preferably formed of the same flexible resin as the rear flange but contains an amount of radiopaque pigment such as barium sulfate sufficient to render the ring opaque to X-rays. Usually the pigment is present in an amount from at least 5% to 35%, generally around 20% by weight.

The front flange 240 of the cartridge 212 can have a bevel 241 so that it is easier to move the front flange 240 past the boss 231 on the body 214 of the device.

The body 214 can also contain a recess 220 placed forward of the rear flange 219 to further protect the valve from failing by further isolating the valve from contacting tissue. A hood may also be provided rearward of the flange 219.

Referring more particularly now to FIG. 5-10 the front flange 240 and the rear flange 244 of the hard cartridge 212 may contain key shaped slots 243, 245 which cooperate with a key bar 265 on the bottom of the soft tubular body 214. The rear end 267 of the key bar 265 bears against the bulbous end 261 of the flexible tab 256.

Referring now to FIGS. 11-14, FIG. 11 illustrates an elastomer flapper valve 10 formed of a valve element 211 spaced from and connected to a surrounding, continuous mounting band 212 by a tab 214 extending from the outer surface 216 of the valve element to inner surface 18 of the band 212. The rigid cartridge 220 shown in FIG. 12 has a groove 222 formed in the outer surface 224 and a slot 226 formed in the distal surface 228 extending from the distal surface 228 to the groove 222. The width of the slot 226 is coextensive with the width of the tab 214. The outer edges of the distal surface 228 is rounded at 230 to prevent tearing of the mounting band 212 as it is assembled with the cartridge 220. The outer edge 232 of the proximal surface of the cartridge 220 can also be chamfered or rounded to prevent tearing of the soft body 234 of the voice prosthesis 236.

Figure 19:
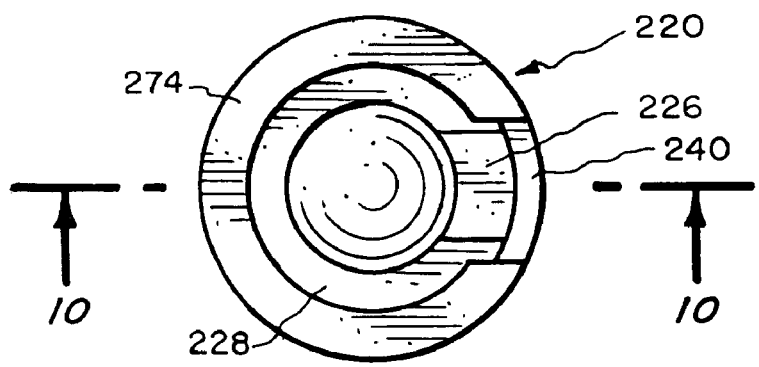
FIG. 19 is a top view in elevation of the cartridge illustrated in FIG. 18.

The cartridge 220 contains a boss 236 extending into the channel 238 through the cartridge forming on its distal surface a seat 240 for the valve element 211. The seats 240 can be disposed normal to the axis of the channel or can be slanted at an angle of 5-10 degrees as illustrated in FIG. 19. The proximal face 242 of the boss 236 can be utilized to engage the distal end of a cleaning brush or insertion tool. The edge 244 of the proximal face 242 can be chamfered.

Referring again to FIGS. 11 to 14 the voice prosthesis 236 is assembled by stretching the band 212 while aligning the tab 214 with the slot 226. The stretched band 212 is then placed over the groove 222 while the tab 214 is seated in the slot 226 against the seat 240 and released into the groove 222. The proximal face 246 of the valve element 211 is reliably seated against the valve seat 240. The valve element 211 may have a dome shape 248 to strengthen the element and prevent wrinkling of the element.

The cartridge-valve assembly 250 is then pushed through the distal end 252 of the soft body 234 until it seats in the annular recess 254 within the soft body 234. The soft body 234 can also contain a conventional distal flange 258 and proximal flange 260 for engaging the surfaces of wall between a trachea and esophagus. The distal flange 260 can contain a radioplaque ring 261 in order to assure that the flange 60 is correctly seated as disclosed in Ser. No. 08/282,277 filed Jul. 27, 1994 now issued as U.S. Pat. No. 5,480,432, the disclosure of which is expressly incorporated herein by reference. The soft body 234 can contain a distal hood 263 to further protect the valve element from being fouled.

Figure 15:
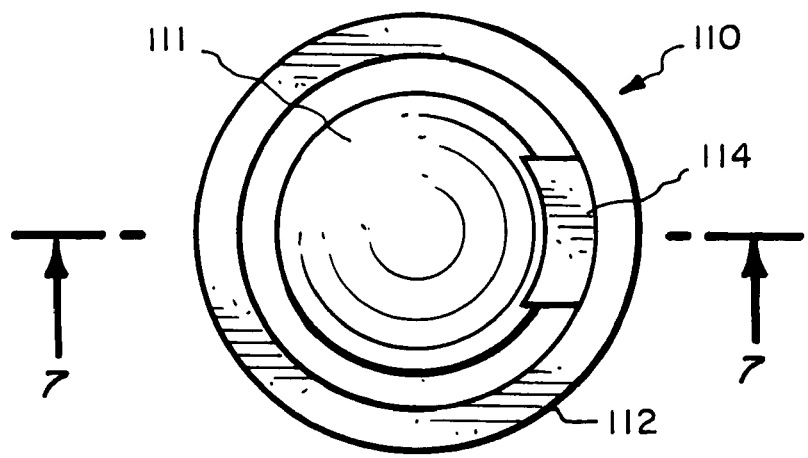
FIG. 15 is a top view in elevation of an alternate embodiment of a valve.
Figure 16:
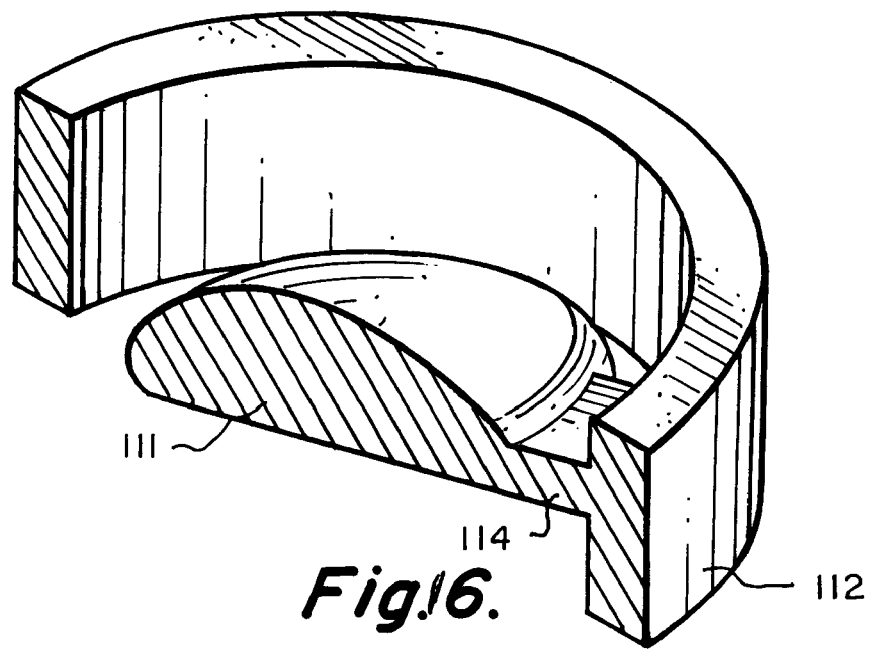
FIG. 16 is a perspective and sectional view of the valve illustrated in FIG. 15.
Figure 17:
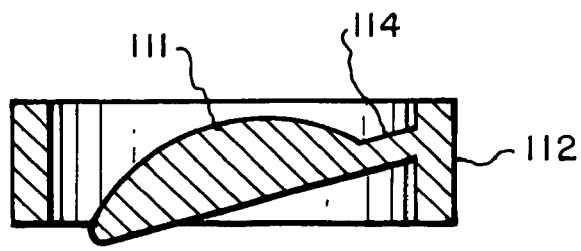
FIG. 17 is a view in section taken along lines 7-7 of FIG. 16.

Referring now to FIGS. 15-17, an alternate embodiment of a valve 310 can be preloaded by forming the tab 314 at an angle from 5 to 20% to a plane normal to the axis of the mounting band 312. The valve element 311 will preload when assembled with a cartridge, not shown.

Figure 18:
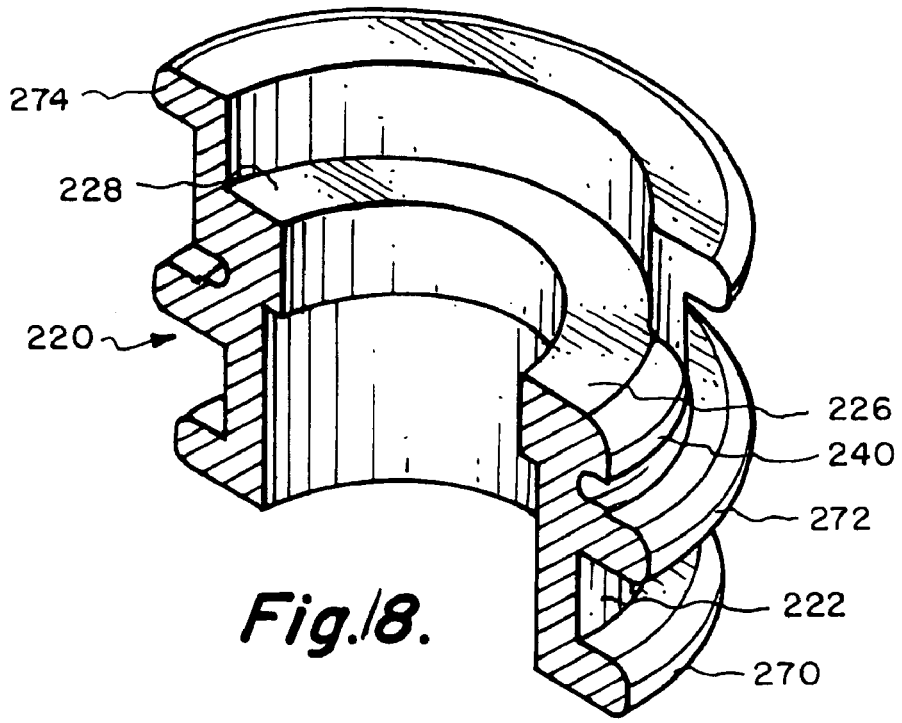
FIG. 18 is a perspective view of an alternate embodiment of a cartridge.
Figure 20:
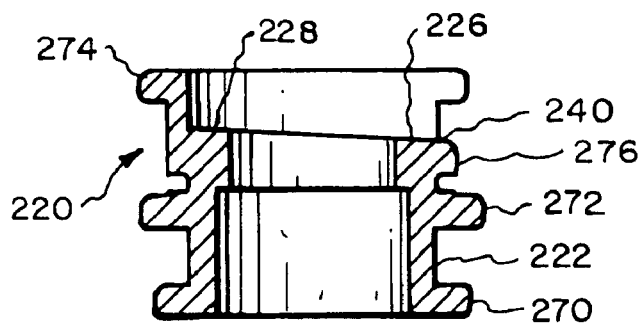
FIG. 20 is a view in section taken along lines 10-10 of FIG. 19.

Referring now to FIGS. 18-20, another way to preload a valve element, not shown, is to form the seating face 340 of a cartridge 320 at an angle of 5-20 degrees by disposing the face 340 at the slot 326 forward of the opposed face 328. The cartridge 320 illustrated in FIGS. 18-20 contains three flanges, a proximal flange 370, a central flange 372 and a distal flange 374 forming a first groove 322 between flanges 372 and 374 for receiving a mounting band of a valve, not shown and a second groove 376 for receiving a cylindrical boss on the body of a prosthesis, not shown, for better securing the assembly of the soft body and the cartridge 320.

Figure 21:
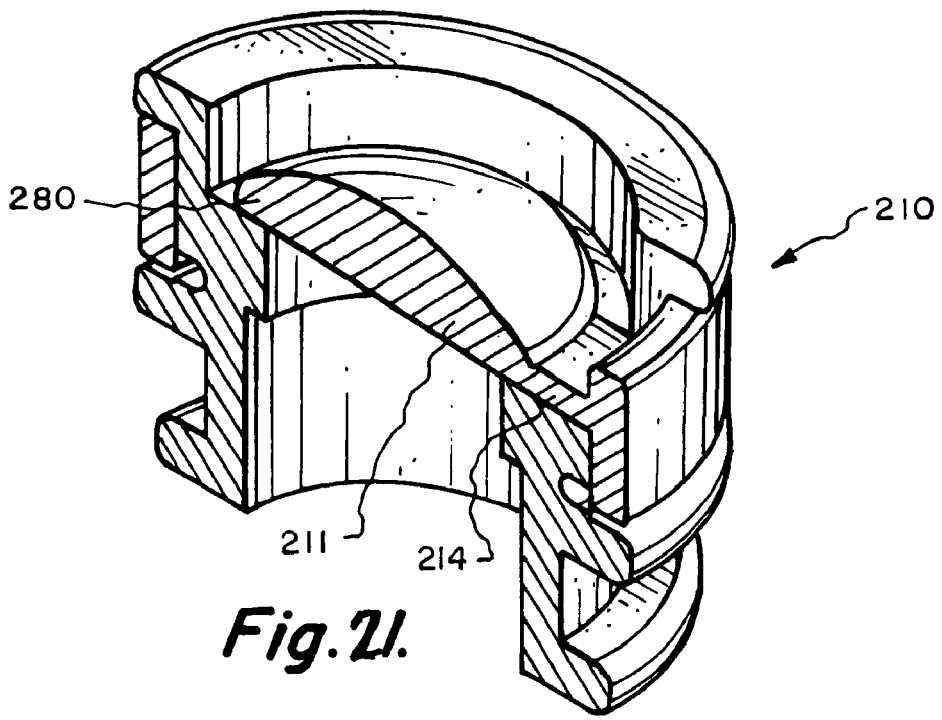
FIG. 21 is a perspective sectional view of the assembly of a valve with the cartridge illustrated in FIG. 18.
Figure 22:
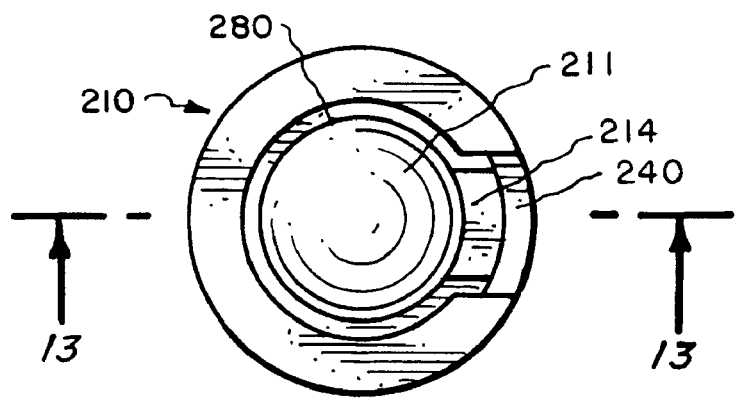
FIG. 22 is a top view in elevation of the assembly illustrated in FIG. 21.
Figure 23:
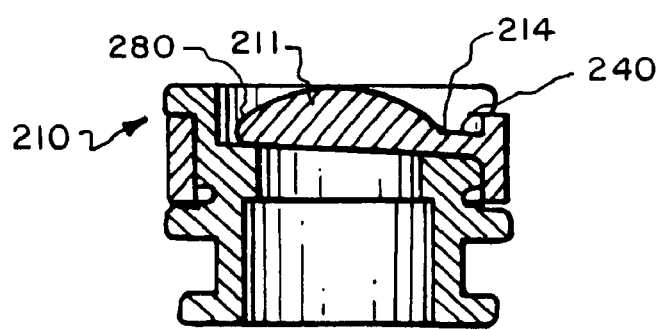
FIG. 23 is a view in sections taken along lines 13-13 of FIG. 22.
Figure 24:
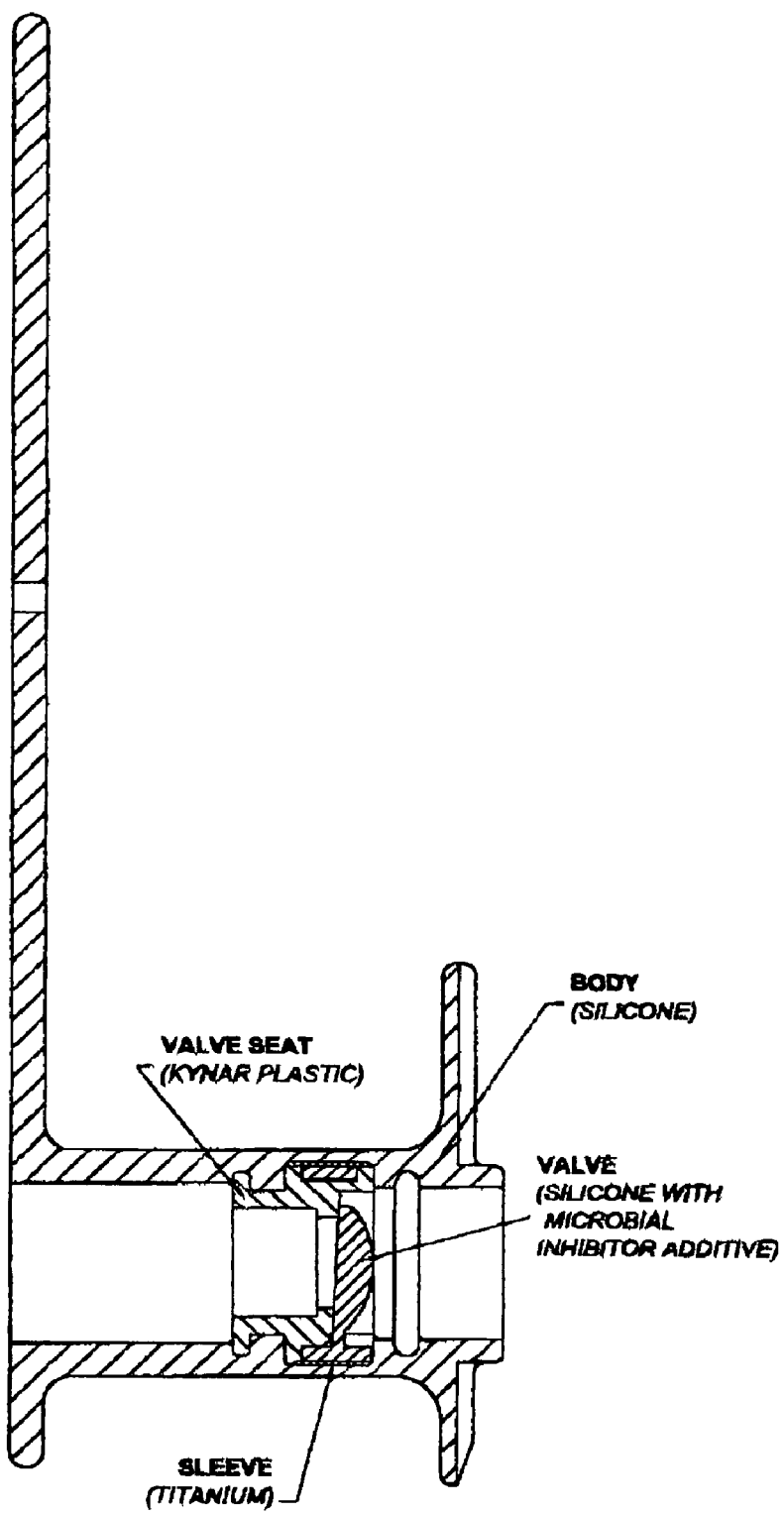
FIG. 24 is a view in section illustrating the use of a metal sleeve to isolate and support the valve.

Referring now to FIGS. 21-23 a valve 410 is illustrated assembled with the cartridge 420. The edge portion 480 of the valve element 411 opposite the tab 414 is preloaded by being faced rearwardly by the slanted seating surface 440.

Providing a microbial resistant valve according to the invention may eliminate or reduce the need to utilize a thick domed valve and a thicker, stiffer rear flange. Since the growth of a thick biofilm layer will be inhibited, warping of the valve is reduced or eliminated. The microbial resistant valve is formed by dispersing a microbial agent such as metal, metal oxide or salt or organic antimicrobial agent into the biocompatible resin.

The preferred manner of providing a surface resistant to microbial growth is to disperse the agent in the resin forming the portion of the device not in direct contact with body tissue. The agent can be inorganic such as a salt or oxide of silver, gold, platinum, zinc or copper, preferably silver oxide or organic materials soluble or dispersible in the resin forming the valve or the cartridge such as hydroxy aromatic carboxylic acids, esters thereof or halogenated phenols. The agent is present in the resin or at least in a surface layer in an amount effective to deter microbial growth and at a concentration that can be toxic to tissue. The portions of the device in contact with tissue can contain a much lower concentration of the microbial agent at a level non-toxic and non-irritating to tissue.

For example, in the case of silver oxide, the concentration of silver oxide effective to deter growth of microbial biofilm is from 1 to 50 phr, preferably 8 to 25 phr. The body of the device which is in direct contact with tissue can be compounded to include from 0.1 to 2 phr, preferably 0.5 to 1.0 phr of silver oxide.

The following experiments were conducted to determine the biocompatibility requirements of compounding silver oxide into bodies and valves of voice prosthesis at different concentrations and of coating the outside surfaces of a voice silicone elastomer prosthesis and valve with vaporized metal coatings by the SPIRE® process. The silver oxide was dispersed in the resin, molded to form a soft voice prosthesis body valve or disc and then cured. The silicone parts were tested in solution proportional to their size.

Cytotoxicity testing was performed on various concentrations of silver oxide and silicone elastomer, and on various combinations of bodies and valves. MEM (Minimum Essential Medium) Elution and Agarose Overlay tests were done. It was decided that the most applicable test, given the use of the voice prosthesis, is the MEM test, as it tends to be more sensitive. The Agarose overlay test is useful to help determine comparative degrees of toxicity for the different percentages of silver oxide.

TESTS PERFORMED

| MATERIAL | AGAROSE OVERLAY | MEM |
| --- | --- | --- |
| 14% Ag$_2$O | | |
| Q7-4750 w/14% Ag$_2$O (valves) | | Nontoxic |
| 10% Ag$_2$O | | |
| 10% Ag$_2$O sample discs | Toxic | |
| 10% Silver sample discs | Nontoxic | |
| Q7-4750 w/10% Ag$_2$O (10 units) | | Nontoxic |
| Q7-4750 w/10% silver (10 units) | | Nontoxic |
| Q7-4750 w/10% Ag$_2$O (valves) | | Nontoxic |
| Q7-4750 w/10% Ag$_2$O (bodies) | Toxic | Toxic |
| Q7-4750 body w/10% Ag$_2$O valve | | Nontoxic |
| 1.0% Ag$_2$O bodies/10.0% valves | | Intermediate |
| 0.5% Ag$_2$O bodies/10.0% valves | | Nontoxic |
| 8% Ag$_2$O | | |
| 0.5% Ag$_2$O bodies/8.0% valves | | Nontoxic |
| 5% Ag$_2$O | | |
| Q7-4750 body w/5% Ag$_2$O valve | | Nontoxic |
| Q7-4750 w/5% Ag$_2$O (bodies) | Toxic | Toxic |
| 2% Ag$_2$O | | |
| Q7-4750 w/2% Ag$_2$O (bodies) | Toxic | Intermediate |
| 0.5% Ag$_2$O | | |
| Q7-4750 w/0.5% Ag$_2$O (bodies) | Nontoxic | Nontoxic |
| 2% Gentian Violet | | |
| Q7-4750 w/2% Gentian violet (discs) | Toxic | |
| 2% Copper Oxide | | |
| Q7-4750 bodies w/2% Copper Oxide valves Q7-4750 control | Nontoxic | Nontoxic |
| Q7-4750 bodies w/2% Copper Oxide valves | | Nontoxic |

The tests showed that 10% silver oxide could be used in the valves if the bodies were straight silicone elastomer, or contain a very low percentage of silver oxide. However, the 10% silver oxide valves seems to be the upper end of toxicity.

The bodies and valves at 10% showed different results. They were tested in solution proportional to their size (theoretically), yet the bodies consistently showed a more toxic response than the valves. A theory is that the bodies simply had a greater mass even when this was compensated for in choosing the solution size, so more silver oxide was able to leach out into the test medium.

Based on these tests, in-vitro test discs were prepared using 5% and 10% silver oxide concentrations, and the clinical voice prosthesis units were prepared using 10% silver oxide valves.

Eight tests were performed using valves of different materials to test for measurable zones of inhibition. Sample discs were prepared of the various materials in the concentrations to be tested. The silver oxide, silver, copper, copper oxide, metallic copper, and gentian violet materials were mixed with silicone elastomer, in the concentrations listed. The SPIRE silver (SPIRE A and B), SPIRE Titanium, SPIRE copper were coatings on the valve using SPIRE's coating method. The novatran is a parylene coating and the BSI is a polyacrylamide coating, both done on the valves.

Cultures of *Candida albicans* were grown up for each test date. The *Candida* cultures were swabbed onto media plates and the sample discs were placed on the plates. The plates were incubated at the specified controlled temperature for 15-24 hours and the plates read for inhibition zones. The plates were then returned to the incubator until overgrown.

All tests were performed under the Class 100 laminar flow bench. Particle counting was performed on the clean bench prior to initiation of the testing.

Summary: Measurable zones of inhibition were demonstrated only on silver oxide, in both the 5% and the 10% concentrations, and on the 2% gentian violet. The zones of inhibition were consistently in the range of 5-7 mm around the test disc.

| TESTING PERFORMED | |
|---|---|
| 1. | |
| Test Samples | Inhibition |
| 10% $Ag_2O$ | Yes |
| 5% $Ag_2O$ | Yes |
| 10% silver | |
| 5% silver | |
| Novatran | |
| BSI | |
| Q7-4750 (control) | |
| 2. | |
| Test Samples | Inhibition |
| New 10% $Ag_2O$ | Yes |
| Old 10% $Ag_2O$ | Yes |
| New 6% silver | |
| Q7-4750 (control) | |
| Old 10% silver xx | | xx Old $Ag_2O$ was taken from a bottle past the expiration date

| 3. | |
|---|---|
| Test Samples* | Inhibition |
| $Ag_2O$ soaked in saline 1 week | Yes |
| SPIRE A | |
| SPIRE B | |

*Candida successfully rinsed off $Ag_2O$ sample, but not off SPIRE samples

| 4. | |
|---|---|
| Test Samples* | Inhibition |
| 0.5% $Ag_2O$ | |
| 1.0% $Ag_2O$ | |
| 5% $Ag_2O$ | |
| Q7-4750 (control) | |
| 10% $Ag_2O$ | |

*No Inhibition; dilutions done incorrectly.
(SPIRE A is a very hydrophilic surface with moderately smooth surface; SPIRE B is a moderate improvement in surface energy with a very smooth surface)

| 5. | |
|---|---|
| Test Samples | Inhibition |
| 5% Cu | |
| 2% Cu | |
| 1% Cu | |
| 10% $Ag_2O$ | Yes |
| Q7-4750 (control) | |
| 5% $Ag_2O$, soaked in saline for 18 weeks | |
| 0.5% $Ag_2O$ | |
| 6. | |
| Test Samples | Inhibition |
| No data recorded (when lab accident occurred) | |
| 7. | |
| Test Samples | Inhibition |
| 10% $Ag_2O$ | Yes |
| 2% copper oxide | |
| SPIRE Ti | |
| SPIRE Cu | |
| 5% Metallic Cu | |
| Domed valve, Q7-4750 | |
| 8. | |
| Test Samples | Inhibition |
| 2% Gentian violet | Yes |
| SPIRE gold | |
| SPIRE Titanium | |
| Q7-4750 (control) | |

Based on the cytoxicity information and the results of the in-vitro tests, it was decided that the clinical units of the silicone elastomer bodies and 10% silver oxide valves, and SPIRE-coated bodies with 10% silver oxide valves would be clinically tested.

Ten patients were given the clinical units under supervision.

| STUDY RESULTS | | | | |
|---|---|---|---|---|
| Patient Number | Control Time | Clinical Unit Time | Increase | Device |
| 1 | 8 days | 49 days | 41 days | 10% $Ag_2O$ |
|   | 27 days | 36 days | 9 days | SPIRE-coated $Ag_2O$ |
| 2 | 59 days | 127 days | 68 days | 10% $Ag_2O$ |
|   | 36 days | | | |
| 3 | 28 days | 69 days | 41 days | 10% $Ag_2O$ |
|   | | 215+ days | 187 days | 10% $Ag_2O$ |
| 4 | 22 days | 258+ days | 236 days | SPIRE-coated |
| 5 | 35 days | 42 days | 7 days | 10% $Ag_2O$ |
|   | | 61 days | 26 days | |
| 6 | 42 days | 13 days | −29 days | 10% $Ag_2O$ |
|   | 42 days | 33 days | −9 days | 10% $Ag_2O$ |
|   | | 38 days | −4 days | 10% $Ag_2O$ |
| 7 | | 26 days | | 10% $Ag_2O$ |
|   | | 4 days | | $Ag_2O$ valve/ SPIRE |
|   | | 10 days | | SPIRE-coated |
| 8 | | 222 days | | 10% $Ag_2O$ |
| 9 | | 296 days | | 10% $Ag_2O$ |
| 10 | | 98 days | | 10% $Ag_2O$ |
|   | | 287+ days | | 10% $Ag_2O$ |

The 27 day sample used by patient #1 had the body SPI-Silicone coated to change its surface characteristics and the valve was silver oxide. Patient #4 used a voice prosthesis which had the body SPI-Silicone coated. Patients #8, #9 and

10 used voice prosthesis with standard silicone bodies and 10% concentration silver oxide valves.

Organic antimircobial are readily and evenly dispersed in resin in amounts usually from 0.2 to 5 percent by weight.

Preferred Percentages of Additives:

|  |  | Preferred |
|---|---|---|
| Triclosan | 0.25 to 5.0% | 0.50 to 3.0% |
| Butyl paraben | 0.25 to 3.0% | 0.50 to 2.0% |

Methods of Introduction:

There are three main methods of introduction of organic additives into the silicone elastomer material. The first method is simply mixing or milling the additives as a powder into silicone elastomer. This is done to either part of a two-part silicone elastomer system or to both parts together prior to molding. The problem with this method is the complete dispersion of the additive in the silicone.

The second method of introduction of the additive into silicone is to pre-dissolve the additive in a minimal amount of isopropanol or other appropriate solvent. This liquid mixture is then mixed or milled into the silicone as described above. The advantage to this method is that there is better dispersion of the additive within the silicone. One disadvantage is that it has been found that the addition of isopropanol negatively affects the physical properties of the finished, cured silicone. These effects are proportional to the amount of isopropanol added and can be minimized to negligible by the addition of only the minimal required isopropanol.

The third method is preferred as it allows dispersion of the additive throughout the silicone without the use of a solvent. This method is simply heating the additive above its melting temperature, but not past the decomposition temperature. It is then mixed into half of the two part silicone at this temperature. The silicone is allowed to cool prior to mixing both parts together and molding. This method provides a uniform distribution of additive throughout the silicone matrix. Additional curing inhibitor such as 2-methyl, 3-butyne-ol.

The following voice prosthesis devices were constructed containing the indicated percent of antimicrobial agent according to the invention. None of the following examples contain any antimicrobial agent in the silicone body.

|  | Valve | % | Cartridge Valve Seat | % |
|---|---|---|---|---|
| 1. | $Ag_2O$ | 2 |  | 0 |
| 2. | $Ag_2O$ | 2 | Triclosan | 2 |
| 3. | Triclosan | 4 | Triclosan | 4 |
| 4. | Butyl Paraben | 2 | Triclosen | 4 |
| 5. | $Ag_2O$ | 2 | Triclosan | 4 |
| 6. | Triclosan | 4 | Triclosan | 4 |
| 7. | Butyl Paraben | 2 | Triclosan | 4 |

Toxicity Testing:

| Test | Results |
|---|---|
| Triclosan: | |
| Cytotoxicity (MEM Elution) on the valve material alone | Toxic |
| Cytotoxicity (MEM Elution) on the device with valve material | Nontoxic |
| Acute Oral Toxicity (7 day observation in the mouse) | Nontoxic |
| Butyl Paraben | |
| Cytotoxicity (MEM Elution) on the device with valve material | Nontoxic |
| Acute Oral Toxicity (7 day observation in the mouse) | Nontoxic |

Zone of Inhibition Data

Preface:

In each of these cases, unless noted, a sample of silicone with respective additive was punched from a slab. The final dimensions of the sample pieces were roughly 5 mm in diameter by 2 mm thick. Each variation of these samples were placed separately in 0.45 saline solution and incubated at 37° C. At the specified time, a sample was taken out of the solution and evaluated for zone of inhibition.

In each of the cases below, the testing organisms was *Candida albicans*, ATCC 10231. The medium used was Sabouraud Dextrose agar. Incubation time was 18 to 24 hours at 37° C. The zone of inhibition test was performed per internal testing standards of Helix Medical, Inc. The base material was Nusil MED 4940 silicone.

The zone of inhibition test technically measures leachability of an antimicrobial from a test article. The samples are placed on a lawn of microbial organisms of choice. As the substance leaches from the test sample, there is a concentration gradient set up as a function diffusion through the sample and diffusion away from the sample. At a certain concentration, a critical concentration, the growth of microorganisms will be greatly reduced. This is manifest as no growth or greatly reduced growth in a radius around the sample. With the purpose of the invention in mind, the size of the zone of inhibition is relatively unimportant, as long as the longevity of the substance with some microbial activity is maintained over time in a soaking condition. The result chosen to signify acceptable antimicrobial activity is inhibition of microbial growth underneath the sample. This signifies that the concentration at the surface of the sample has retained at least the critical concentration of antimicrobial substance. If the surface concentration can be maintained at or above the critical concentration, then little to no growth will colonize on the surface of this material.

Note: For inhibition underneath sample, it is measured either as Inhibition (I), Partial Inhibition (PI), or No Inhibition (NI).

Triclosan 0.5%:

| Time Soaked (weeks) | Zone of Inhibition (mm) | Inhibition Underneath Sample (I, PI, NI) |
|---|---|---|
| 1 day | 0 | I |
| 1 | 0 | I |
| 2 | 0 | I |
| 3 | 0 | I |
| 4 | 0 | I |

Triclosan 1.0%:

| Time Soaked (weeks) | Zone of Inhibition (mm) | Inhibition Underneath Sample (I, PI, NI) |
|---|---|---|
| 12 | 0 | I |
| 16 | 0 | I |

Triclosan 2.0%:

| Time Soaked (weeks) | Zone of Inhibition (mm) | Inhibition Underneath Sample (I, PI, NI) |
|---|---|---|
| 1 day | 1 | I |
| 1 | 1 | I |
| 2 | 1 | I |
| 3 | 1 | I |
| 4 | 1 | I |
| 8 | 1 | I |
| 12 | 1 | I |
| 16 | 0.5 | I |

Triclosan 2.0% molded valves:

| Time Soaked (weeks) | Zone of Inhibition (mm) | Inhibition Underneath Sample (I, PI, NI) |
|---|---|---|
| 1 Day | 1 | I |
| 1 | 1 | I |
| 2 | 1 | I |
| 3 | 1 | I |
| 11 | 1 | I |
| 12 | 1 | I |
| 16 | 1 | I |
| 20 | 1 | I |
| 24 | 1 | I |

Butyl paraben 1%:

| Time Soaked (weeks) | Zone of Inhibition (mm) | Inhibition Underneath Sample (I, PI, NI) |
|---|---|---|
| 1 day | 1 | I |
| 1 | 1 | I |
| 2 | 1 | I |
| 3 | 1 | I |
| 4 | 1 | I |
| 8 | 1 | I |

Butyl paraben 1%:

| Time Soaked (weeks) | Zone of Inhibition (mm) | Inhibition Underneath Sample (I, PI, NI) |
|---|---|---|
| 1 Day | 1.5 | I |
| 1 | 1.5 | I |
| 2 | 1.5 | I |
| 3 | 2 | I |
| 4 | 2 | I |
| 8 | 2 | I |
| 12 | 1 | I |
| 16 | 1 | I |

Butyl Paraben 1% molded valves:

| Time Soaked (weeks) | Zone of Inhibition (mm) | Inhibition Underneath Sample (I, PI, NI) |
|---|---|---|
| 1 Day | 0 | I |
| 1 | 0 | I |
| 2 | 0 | I |
| 3 | 0 | I |
| 4 | 0 | I |
| 8 | 0 | PI |

Voice prosthesis formed with microbial resistant valves will be able to be used for much longer periods without the need to remove the prosthesis for cleaning. The prosthesis can be made with thinner valves, body and flanges since there is no need to be as stiff and rigid to avoid bending and wrinkling due to growth of *Candida Albicans*. The body of the voice prosthesis can also be compounded with antimicrobial agents at a level acceptable to the FDA.

The Indwelling Low Pressure Voice Prosthesis of the invention is designed for those persons who are unable or resistant to changing the voice prosthesis every two or three days as was recommended for the non-indwelling, patient-removable Low Pressure Voice Prosthesis. The Indwelling Low Pressure Voice Prosthesis has been specifically designed to maintain the placement of the prosthesis in the tracheoesophageal puncture so that routine changing of the device is not necessary.

It is to be realized that only preferred embodiments of the invention have been described and that numerous substitutions, modifications and alterations are permissible without departing from the spirit and scope of the invention as defined in the following claims.

The invention claimed is:
1. A voice prosthesis device comprising:
 a first body having a first central tubular channel comprising a medical grade elastomer, wherein at least a portion of an external surface of said first body is in direct contact with tissue when disposed in vivo; and
 a second body disposed within said first central tubular channel of said first body, wherein said second body defines a second tubular channel and comprises a rear flange that forms a rigid valve seat, a valve flap, and a flexible hinge, wherein said valve flap is connected to said flexible hinge and is operable to seal and open said second tubular channel; wherein said valve flap and said hinge do not contact tissue when disposed in vivo and are formed of a medical grade silicone elastomer material having an antimicrobial agent dispersed therein, and wherein said antimicrobial agent is present at a concentration effective to deter microbial growth so that the flap reliably seals against said rigid valve seat.
2. The voice prosthesis according to claim 1, wherein said second body forming said rear flange further defines an outer surface having a groove formed therein and said flexible hinge is connected to an outer mounting band, wherein said groove in said outer surface receives said outer mounting band to mount said hinge and said valve flap therein to seal said valve seat.

3. The voice prosthesis device according to claim 1 in which the antimicrobial agent is selected from the group consisting of (a) antimicrobial inorganic particles of metals, metal oxides, metal salts, and metal halides and (b) organic antimicrobial materials.

4. The voice prosthesis device according to claim 3 in which the organic antimicrobial material is selected from the group consisting of (a) unsaturated aliphatic acid salts, (b) halogenated hydroxy aromatic acids, (c) esters thereof, and (d) aromatic ethers.

5. The voice prosthesis device according to claim 3 in which the metal, salt or oxide thereof is present in an amount from 5 to 50 phr or the organic antimicrobial material is present in an amount from 0.2 to 5% by weight.

6. The prosthesis device according to claim 3 in which the organic antimicrobial material is selected from the group consisting of butyl paraben and trisclosan.

7. The prosthesis device according to claim 3 in which the inorganic particles comprise silver oxide.

8. The voice prosthesis device according to claim 1 in which the valve is mounted within a hard cartridge.

9. A voice prosthesis for use in contact with tissue, comprising:
   a tubular body having a central channel and an annular wall having an inside surface not in contact with tissue and an outside surface in contact with tissue when disposed in vivo;
   a valve-cartridge assembly disposed in said central channel and comprising a rigid cartridge element and an elastomeric valve element, wherein said rigid cartridge element has an outer surface having a receiving groove and said valve element comprises a valve flap connected to an outer mounting band, wherein said receiving groove receives said outer mounting band of the valve element, which is operable to seal and intermittently open said central channel of said tubular body; wherein said valve element comprises an elastomer material having a dispersion of agent throughout the valve element at a level that is effective to retard microbial growth.

10. The voices prosthesis according to claim 9 in which said tubular body and said valve element are formed of a molded silicone elastomer.

11. The voice prosthesis according to claim 9 in which the agent comprises an antimicrobial material that is selected from metal salts, metal oxides and organic antimicrobial materials.

12. The voice prosthesis according to claim 11 in which the antimicrobial material is selected from silver oxide in amount from 6 to at least 50 phr or butyl paraben or triclosan in an amount from 0.2 to 5% by weight dispersed in the elastomer forming the valve element.

13. The voice prosthesis according to claim 10 in which the prosthesis further includes a metal sleeve mounted on the rigid cartridge element.

14. A method of uniformly dispersing a silver oxide antimicrobial agent into a silicone resin material, wherein said silver oxide alters a work-time of the silicone resin material; adding silver oxide particles to said silicone resin material mixture; adding a polymerization inhibitor to said silicone resin material before molding a component of a voice prosthesis device; and curing the resin material to form the component.

15. A method of increasing the life of a valve having an outside surface not in contact with tissue, the valve being mounted on a cartridge or a ring that has an inside surface not in contact with tissue and that is disposed in a channel through the body of a voice prosthesis, the outside surface of the body being in direct contact with the tissue when disposed in vivo, the method comprising:
   forming a valve having antimicrobial activity by dispersing an inorganic or organic antimicrobial agent at a level that is effective to retard detrimental microbial growth in a biocompatible resin to form a mixture that is molded to form the valve therefrom; and
   disposing the valve within said channel.

16. The method according to claim 15 in which the method further comprises providing antimicrobial activity in at least one of the cartridge or ring by dispersing into a biocompatible resin used to form the cartridge or ring an antimicrobial agent or agents at a level that is effective to retard detrimental microbial growth and forming the cartridge or ring therefrom.

* * * * *

UNITED STATES PATENT AND TRADEMARK OFFICE
CERTIFICATE OF CORRECTION

| | |
|---|---|
| PATENT NO. | : 7,520,897 B2 |
| APPLICATION NO. | : 10/990168 |
| DATED | : April 21, 2009 |
| INVENTOR(S) | : Seder et al. |

It is certified that error appears in the above-identified patent and that said Letters Patent is hereby corrected as shown below:

Col. 16, line 64 (Claim 1): "the flap" should be -- the valve flap --

Col. 17, line 20 (Claim 6): "prosthesis" should be -- prosthetic --

Col. 17, line 23 (Claim 7): "prosthesis" should be -- prosthetic --

Col. 18, line 1 (Claim 10): "voices" should be -- voice --

Signed and Sealed this

Sixteenth Day of March, 2010

David J. Kappos
*Director of the United States Patent and Trademark Office*